US 6,444,445 B2

(12) United States Patent
Nikolich et al.

(10) Patent No.: US 6,444,445 B2
(45) Date of Patent: *Sep. 3, 2002

(54) LIVE VACCINE AGAINST BRUCELLOSIS

(75) Inventors: Mikeljon P. Nikolich, Takoma Park; David L. Hoover, Rockville, both of MD (US); Richard L. Warren, Blue Bell, PA (US); Luther E. Lindler, Wheaton; Ted L. Hadfield, Colesville, both of MD (US); Gerhardt G. Schurig, Blacksburg, VA (US); Stephen M. Boyle, Blacksburg, VA (US); John R. McOulston, Blacksburg, VA (US); Nammalwar Sriranganathan, Blacksburg, VA (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/010,877

(22) Filed: Jan. 22, 1998

(51) Int. Cl.$^7$ ................................................. C12P 21/06
(52) U.S. Cl. ................ 435/69.3; 435/69.1; 435/71.1; 435/71.2; 435/172.1; 435/320.1; 435/243; 536/23.1; 536/23.7; 536/24.32; 536/24.1; 424/252.1
(58) Field of Search ............................... 536/23.1, 23.7, 536/24, 32, 24.1; 435/69.1, 69.3, 71.1, 320.1, 71.2, 172.1; 424/252.1

(56) References Cited

U.S. PATENT DOCUMENTS 5,643,771 A    7/1997   Stocker

OTHER PUBLICATIONS

Winter, A. J. et al. (1996) Protection of BALB/c mice against homologous and heterologous species of *Brucella* by rough strain vaccines derived from *Brucella melitensis* and *Brucella suis* biovar 4. Amer. J. Vet. Res. 57:677–683.

McQuiston, J.R. et al. (1995) Identification of the *rfb U* gene of *Brucella abortus* and the creation of VTRM1, VTRA1 and VTRS1. Abstract, CRWAD, Nov. 1995.

McQuiston, J.R. et al. (1995) Creation of rough *Brucella* mutants using allelic replacement of the *rfbU* gene encoding mannosyl transferase. Abstract. CRWAD, Nov. 1995.

PCT Invitation to Pay Additional Fees and partial International Search Report, dated Sep. 2, 1999, in PCT/US99/01284 (Intl. filing date Jan. 21, 1999), 3 pages.

Leal–Klevezas et al., "Molecular Detection of Brucella spp.: Rapid Identification of B.abortus biovar I Using PCR," Archives of Medical Research, vol. 26, No. 3, pp. 263–267 (1995).

Cheville et al., "Bacterial Persistence and Immunity in Goats Vaccinates with a purE Deletion Mutant or the Parental 16M Strain of *Brucella melitensis*," Infection and Immunity, vol. 64, No. 7, pp. 2431–2439 (Jul., 1996).

Liu et al., "Glycosyl Transferases of O–Antigen Biosynthesis in *Salmonella enterica*: identification and Characterization of Transferase Genes of Groups B, C2 and E1," Journal of Bacteriology, vol. 175, No. 11, pp. 3408–3413 (Jun. 1993).

Winter et al., "Protection of BALB/c mice against homologous and heterologous species of Brucella by rough strain vaccines derived from *Brucella melitensis* and *Brucella suis* biovar 4," AJVR, vol. 57, No. 5, pp. 677–683 (May, 1996).

de Bagues et al., "An ELISA with *Brucella lipopolysaccharide* antigen for the diagnosis of B, melitensis infection . . . B. melitensis strain Rev 1 vaccination", Veterinary Microbiology, 30 (1992) 233–241.

Corner and Alton, "Persistance of *Brucella abortus* strain 19 infection in adult cattle vaccinated with reduced doses", Res. in Veterinary Science, 1981, 31, 342–344.

Drazek et al, "Deletion of purE Attenuates *Brucella melitensis* 16M for Growth in Human Monocyte–Derived Macrophages", Infection and Immunity, vol. 63, No. 9, Sep. 1995, pp. 3297–3301.

de Bagues et al., "Vaccination with *Brucella abortus* Rough Mutant RB51 Protects BALB/c Mice against Virulent STrains of *Brucella abortus, Brucella melitensis* and *Brucella ovis*", Infection and Immunity, vol. 62, No. 11, Nov. 1994, pp. 4990–4996.

de Bagues et al., "Responses of ewes to B. melitensis Rev 1 vaccine administered by subcutaneous or conjunctival routes at different stages of pregnancy", Ann. Rech, Vet. (1989) 20, 205–312.

Pardon et al., "Serological and allergic reactions of ewes after silmultaneous vaccinations with two living attenuated strains of Brucella and Salmonella", Ann Rech. Vet. (1990) 21, 153–160.

Chapter 6, Prevention, "Strain 19 Vaccine", from Brucellosis Research: an evluation, Report of the subcommittee on Brucellosis research, National Academy of Sciences, Washington, D.C., National Academy Press, 1977, 61–77.

(List continued on next page.)

Primary Examiner—Jennifer E. Graser
(74) Attorney, Agent, or Firm—Elizabeth Arwine; Charles H. Harris

(57) ABSTRACT

Live Brucella vaccines and methods for preparing the live vaccines protective against brucellosis are described. The vaccines are prepared by introducing a deletion in the rfbU gene of a strain of Brucella which results in attenuation of the strain while retaining the desired immunogenicity to initiate a protective immunogenic response. Other strains with varying levels of attenuation are described.

13 Claims, 2 Drawing Sheets

OTHER PUBLICATIONS

Schurig et al., "Biological properties of RE51; a stable rough strain of *Brucella abortus*", Vet. Microbiology, 28 (1991) 171–188.

Winter et al., "Protection of BALB/c mice against homologous and heterologous species of Brucella by rough strain vaccines derived from *Brucella melitensis* and *Brucella suis* biovar 4," AJVR, vol. 57, No. 5, May 1996, 677–683.

Cheville et al., "Immune responses and protection against infection and abotion in cattle experimentally vaccinated with mutant strains of *Brucella abortus*", Am J Vet Res., vol. 54, No. 10, Oct. 1993, 1591–1597.

Liu et al., "Glycosyl Transferases of O–Antigen Biosynthesis in *Balmonella enterica:* Identification and Characterization of Transferase Genes of Groups B, C2 and E1", J. Bacteriology, Jun. 1993, vol. 175, No. 11, pp. 3408–3413.

"Brucellosis: An Overview", 1st International Conference on Emerging Zoonoses, Jerusalem, Israel, vol. 3, No. 2, Apr.–Jun. 1997, pp. 213–221.

Young, E., "Human Brucellosis", Review Articles, Reviews of Infectious Diseases, vol. 5, No. 5, Sep.–Oct., 1983, pp. 821–842.

Blasco and Diaz, "*Brucella melitensis* Rev–1 vaccine as a cause of humand brucellosis", The Lancet, vol. 342, Sep. 25, 1993, 685–688.

McQuiston et al., "Creation of rough Brucella mutants using allelic replacement of the rfbU gene encoding mannosyl transferase", CRWAD, 1995, (Abstract) 2 pages.

Rigby and Fraser, "Plasmid Transfer and Plasmid–mediated Genetic Exchange in *Brucella abortus*", Can J Vet Res, 1989, vol. 53, pp. 326–330.

SEQUENCE LISTING

<160> NUMBER OF SEQ ID NOS: 6

<210> SEQ ID NO 1
<211> LENGTH: 2693
<212> TYPE: DNA
<213> ORGANISM: Brucella abortus
<220> FEATURE:

<400> SEQUENCE: 1

```
caccttatgt ttgggacatt ttaattagga acgtttatgc        40
cttcggatgc cgtgggcgtg gcatccgcat gagggatggc        80
tttgcgtttc tgcgctttga agatgttgaa attgggttag       120
ggccgcaata tggtggtgta agcctaccag catatgagtt       160
tcgaaatttt gaggggttat ttcttcgccg caccgaagcc       200
actggattgg atggatatac agaccttgga tacgtcccag       240
atgctgaaca gcgggggttc atctttgcag acggagcagc       280
cctccacatc aatagcctgt ttgcagataa taacaagggt       320
gatggcgtgt tttgccaaaa cgtccaatac gtagatggaa       360
acgatctcaa ttcatccatc gacggcggaa ctgggttcaa       400
ttttatcaac gtagatcgca taaacatcaa tacgatccgc       440
agtggtggcc gccggaatat ggcaccagga aatcttaaca       480
ctgtttccca aggtatctct ttgaatgcaa attgtcagac       520
tgtaattata ggcaacgcag ttacccacaa ctggtgaagt       560
cacggttttt atagccaagc tcaggacatt ttggttaatg       600
gtctgatatc acgtgataat ggcggaaggg ggtacgttgc       640
agagggttca gcagggtcat ctctcctaaa tggggccgtt       680
ttcagagata atgtagcagg gaattatttt acaggaggga       720
caagcgtaaa ccatctcgcg aacctccaac ttcataactc       760
tagcaccggg gggaaaactt ttgtggccaa tgtcaccaca       800
aatgggtctg cataacggtc cttgccattt taactataaa       840
tgagctattc ccgcgcatta agagtagaca cgggaaatca       880
gtatggctcc gagacatatt acagttatcc taccagttaa       920
gtaccgaggc ggaagtcttc gagttacgaa gaatatcgtt       960
cgaatgcttt tgaagggaag tcagaattat ggtgaacagt      1000
gtcaagttag attggcagta cgtgccgata cctacgatat      1040
tggggaggag tttcgtgatc ttatcgataa tggtgtagag      1080
gttcgggaaa tatcattcaa agaagttcct ccagaagatg      1120
ttaacaatgc taactatttc caaggtagaa atatcgacct      1160
acagtcgaga acctattggc taatggagga tggccaaaac      1200
aactgtgccg atagtgacct ttggctagtt gtatcctact      1240
ctgtagagta tcctattgcc ccaataaggc cgactctgat      1280
atttgccacc gatttcattc aaaggtacgt acctgatatt      1320
```

-continued

| | |
|---|---|
| atttggccac cacggcccgg tgaggggat gctgaggctc | 1360 |
| ttgcgttctt acgacaatca gacggcgtac tagctacaac | 1400 |
| accacacacg cggctggatg cgatttcata cgctggctta | 1440 |
| cctgcgtcca aagtttatct tgctccgatg gagtttgacc | 1480 |
| cgacgttttt ggatcgttac cggtcagtgt ctaaggttaa | 1520 |
| ggaaccctat ttcctttggc caaccaaccc aaatgctcac | 1560 |
| aaaaaccatg caaaagcgtt tcaagcgcta gacctatatt | 1600 |
| acggcaaact aaagggtaag ataaagacaa agatagtcgg | 1640 |
| tgtgagtagt gtgcggatgg acccatccca tcgatggcag | 1680 |
| gccaagtacg aaaataaggc ttatgtgaaa tctgtacggg | 1720 |
| aaattgttgc gggtctcgac aacctgaaaa gcaatgttga | 1760 |
| gttcgctggt gaggttgcgg acaaggagta tgcggagctt | 1800 |
| cttgcttcag cttgtttctt ttggcatcca actttggcag | 1840 |
| acaacggaac ttttgctgcg gtcgaagcag catatatggg | 1880 |
| atgtccaacg cttttcaaacg actacccgca gatgcggtat | 1920 |
| atttctaacc gtttcgaaat tcccatgcag tattttaacg | 1960 |
| caaggtctgt gaaggaaatg gcatcagcgc ttaagcaaat | 2000 |
| ggaggagacg ccaatagatg taggtttatt gccaagtcga | 2040 |
| gaaaccctat ctctgcattc gtgggaagct cacgcttccg | 2080 |
| aatactggga tgtgatcgtg agggcagcgg catgaataag | 2120 |
| ctcggcgtgt ttatcggcta aacccaggc caattagatc | 2160 |
| catatcaggg tatttctcgc ttaattgcat tcgtgatcaa | 2200 |
| ggggcccttg aaccagggta gcggtgtaac aattgcttgc | 2240 |
| cccggctggc taaggacga tgtacgtgtt ctttgggaag | 2280 |
| atgctgatat cccacttgaa gcggtcaaaa ttatcgcgac | 2320 |
| gaatggtcag cctccattgg cttcgttatg gaagttgaga | 2360 |
| gataagttcc gtaagagacg gacgagtaaa cgaaaacgtc | 2400 |
| tctggctgga gcgctatgga aaaaatgttg caaattttgt | 2440 |
| tgcagaatgg cttctttcgc gctcgtattg ggggattttt | 2480 |
| ttgggggctg ctgcaattgc tgtagtgact attctacttg | 2520 |
| ccgtaccaat tgctatagcc ttcaccgctc ttatcggcct | 2560 |
| tctatttgct cgtcggctta ttagacgtgt tatcaggtca | 2600 |
| aagcttggtt tgttttttca caaaaatgcc aatcaattca | 2640 |
| acaaattaat gtcatctgat gaaaccatcg accggatgag | 2680 |
| ggaacgggaa ttc | 2693 |

<210> SEQ ID NO 2
<211> LENGTH: 410
<212> TYPE: PRT
<213> ORGANISM: Brucella abortus

<400> SEQUENCE: 2

Met Ala Pro Arg His Ile Thr Val Ile Leu

-continued

```
                    5                   10
Pro Val Lys Tyr Arg Gly Gly Ser Leu Arg
                   15                   20
Val Thr Lys Asn Ile Val Arg Met Leu Leu
                   25                   30
Lys Gly Ser Gln Asn Tyr Gly Glu Gln Cys
                   35                   40
Gln Val Arg Leu Ala Val Arg Ala Asp Thr
                   45                   50
Tyr Asp Ile Gly Glu Glu Phe Arg Asp Leu
                   55                   60
Ile Asp Asn Gly Val Glu Val Arg Glu Ile
                   65                   70
Ser Phe Lys Glu Val Pro Pro Glu Asp Val
                   75                   80
Asn Asn Ala Asn Tyr Phe Gln Gly Arg Asn
                   85                   90
Ile Asp Leu Gln Ser Arg Thr Tyr Trp Leu
                   95                  100
Met Glu Asp Gly Gln Asn Asn Cys Ala Asp
                  105                  110
Ser Asp Leu Trp Leu Val Val Ser Tyr Ser
                  115                  120
Val Glu Tyr Pro Ile Ala Pro Ile Arg Pro
                  125                  130
Thr Leu Ile Phe Ala Thr Asp Phe Ile Gln
                  135                  140
Arg Tyr Val Pro Asp Ile Ile Trp Pro Pro
                  145                  150
Arg Pro Gly Glu Gly Asp Ala Glu Ala Leu
                  155                  160
Ala Phe Leu Arg Gln Ser Asp Gly Val Leu
                  165                  170
Ala Thr Thr Pro His Thr Arg Leu Asp Ala
                  175                  180
Ile Ser Tyr Ala Gly Leu Pro Ala Ser Lys
                  185                  190
Val Tyr Leu Ala Pro Met Glu Phe Asp Pro
                  195                  200
Thr Phe Leu Asp Arg Tyr Arg Ser Val Ser
                  205                  210
Lys Val Lys Glu Pro Tyr Phe Leu Trp Pro
                  215                  220
Thr Asn Pro Asn Ala His Lys Asn His Ala
                  225                  230
Lys Ala Phe Gln Ala Leu Asp Leu Tyr Tyr
                  235                  240
Gly Lys Leu Lys Gly Lys Ile Lys Thr Lys
                  245                  250
Ile Val Gly Val Ser Ser Val Arg Met Asp
                  255                  260
Pro Ser His Arg Trp Gln Ala Lys Tyr Glu
                  265                  270
```

```
Asn Lys Ala Tyr Val Lys Ser Val Arg Glu
            275                 280

Ile Val Ala Gly Leu Asp Asn Leu Lys Ser
            285                 290

Asn Val Glu Phe Ala Gly Glu Val Ala Asp
            295                 300

Lys Glu Tyr Ala Glu Leu Leu Ala Ser Ala
            305                 310

Cys Phe Phe Trp His Pro Thr Leu Ala Asp
            315                 320

Asn Gly Thr Phe Ala Ala Val Glu Ala Ala
            325                 330

Tyr Met Gly Cys Pro Thr Leu Ser Asn Asp
            335                 340

Tyr Pro Gln Met Arg Tyr Ile Ser Asn Arg
            345                 350

Phe Glu Ile Pro Met Gln Tyr Phe Asn Ala
            355                 360

Arg Ser Val Lys Glu Met Ala Ser Ala Leu
            365                 370

Lys Gln Met Glu Glu Thr Pro Ile Asp Val
            375                 380

Gly Leu Leu Pro Ser Arg glu Thr Leu Ser
            385                 390

Leu His Ser Trp Glu Ala His Ala Ser Glu
            395                 400

Tyr Trp Asp Val Ile Val Arg Ala Ala Ala
            405                 410

<210> SEQ ID NO 3
<211> LENGTH: 31
<212> TYPE: DNA
<213> ORGANISM: Brucella melitensis

<400> SEQUENCE: 3
ggatgtcgac ccagccctcc acatcaatag c                              31

<210> SEQ ID NO 4
<211> LENGTH: 30
<212> TYPE: DNA
<213> ORGANISM: Brucella melitensis
<220> FEATURE:

<400> SEQUENCE: 4
ttgcggatcc tttactcgtc cgtctcttac                                30

<210> SEQ ID NO 5
<211> LENGTH: 18
<212> TYPE: DNA
<213> ORGANISM: Brucella melitensis
<220> FEATURE:

<400> SEQUENCE: 5
caccatgcag ccgacaca                                             18

<210> SEQ ID NO 6
<211> LENGTH: 18
<212> TYPE: DNA
```

```
<213> ORGANISM: Brucella melitensis
<220> FEATURE:

<400> SEQUENCE: 6
ccgcgccgca gattcagg                                                      18
```

LIVE VACCINE AGAINST BRUCELLOSIS

Brucella infects a significant number of people and livestock in developing countries and infects wild as well as domestic animals in the United States. In addition, Brucella is a potential biowarfare agent; strains of Brucella have been constructed with resistance to multiple antibiotics used to treat the disease. These strains pose a significant morbidity and mortality threat to exposed personnel. Brucellosis symptoms include recurring fever, chills and anxiety. Even though the disease is rarely fatal, once well established, the disease is difficult to treat since the bacteria reside in the bone marrow.

Two live attenuated Brucella strains currently approved for use as animal vaccines, *B. abortus* Strain 19 [Cheville, et al. (1993) *Am. J. Vet. Res.* 54:1591-1597; *Brucellosis research: an evaluation.* Report of the subcommittee on Brucellosis Research, National Academy of Sciences. Washington, D.C.: National Academy Press, 1977:61-77] and *B. melitensis* strain Rev 1 [Jimenez de Bagues, M. P. et al. (1989) *Ann. Rech. Vet.* 20:205-213; Pardon, P. et al. (1990) *Ann. Rech. Vet.* 21:153-160], are not ideal vaccine strains. Both strains cause vaccinated animals to seroconvert and thus make subsequent serological diagnosis of brucellosis difficult [Jimenez de Bagues, M. P. et al. (1992) *Vet. Microbiol.* 30:233-241]. Both strains can induce abortion (Jimenez de Bagues, 1989, supra; Corner, L. A. and Alton G. G. (1981) *Res. Vet. Sci.* 31:342-344] and both can cause disease in humans [Blasco, J. M. and R. Diaz (1993) *Lancet* 342:805; Young, E. J. (1983) *Rev. Inf. Dis.* 5:821-842]. A more recent attenuated strain of *B. abortus*, RB51 [Schurig, G. G. et al. (1991) *Vet. Microbiol.* 28:171-188], shows more promise as a live vaccine strain. RB51 is a rough strain that confers protection against infection by Brucella, yet does not cause seroconversion [Cheville, N. F. 1993, supra; Jimenez de Bagues, M. P. et al. (1994) *Infect. Immun.* 62:4990-4996]. However, neither the genetic basis of the RB51 rough mutation nor the basis of attenuation is known. Also, RB51 carries resistance to rifampin, an antibiotic currently used to treat brucellosis.

Therefore, there is a need for a live attenuated Brucella vaccine strain, with a defined nonreverting genetic mutation, which does not cause seroconversion in the vaccinee, and which does not retain resistance to antibiotics used in the treatment of brucellosis.

SUMMARY OF THE INVENTION

The present invention fulfills the need described above. In this application is described attenuated rough strains of Brucella, containing genetically defined mutations, which will not cause seroconversion. The mutations in these attenuated Brucella strains were created by DNA deletion, the type of mutation least susceptible to genetic reversion and are therefore advantageous as vaccine strains. These vaccines strains do not retain resistance to an antibiotic useful for treatment of brucellosis.

More specifically, this invention relates to two genetically defined rough mutants of *Brucella melitensis*, WRR51 and WRRP1, as candidate strains for a live vaccine against brucellosis. These strains differ from Brucella live vaccines currently used in livestock because they have genetically defined mutations that were created by deleting DNA from the Brucella chromosome. Both strains have a lipopolysaccharide (LPS) defect and thus do not cause the seroconversion that complicates disease screening. Smooth strains currently approved for use in animals are not good candidates for human vaccines because though attenuated, they can still cause disease in humans. One of the vaccine strains of the present invention, WRRP1, is a double deletion mutant that is highly attenuated and is unlikely to cause disease in humans.

Briefly, the genetically defined rough mutants of Brucella were constructed by using a *Brucella abortus* VTRA1 chromosome containing a Tn5 insertion which conferred a rough phenotype [Winter, A. J. et al. (1996) *Amer. J. Vet. Res.* 57:677-683]. The *B. abortus* gene containing the Tn5 insertion was cloned from the VTRA1 chromosome and the nucleotide sequence of the 2693 bp (SEQ ID NO:1) region containing the transposon insertion was determined. The Tn5 insertion was found to be located within an open reading frame of 1233 bp spanning nucleotides 883 through 2115 of SEQ ID NO:1 which coded for a gene that was distantly related (40% amino acid similarity) to the sequence of the *Salmonella enterica* LT2 rfbU, a gene encoding a mannosyltransferase [Liu, D. et al. (1993) *J. Bacteriol.* 175:3408-2414]. A deletion of 607 bp was made in the putative rfbU gene and a cassette containing a chloramphenicol acetyl transferase gene (cat) was ligated into the deletion site to create rfbU/cat. The plasmid containing rfbU/cat, pRFBU1, was electroporated into *B. melitensis* strain 16M and electroporants with pRFBU1 integrated were selected on Brucella agar containing chloramphenicol. Southern DNA hybridization confirmed that the chloramphenicol resistant and ampicillin sensitive electroporants had the deletion mutation carrying the chloramphenicol resistance cassette in place of the wild type chromosomal locus resulting from a directed allelic exchange by a double crossover recombinational event. The deletion strain, designated WRR51, was confirmed to be rough by staining with crystal violet, and by lack of agglutination with an anti-LPS serum.

A purE deletion was then introduced into *B. melitensis* strain WRR51 by a similar allelic exchange procedure. PurE is an essential enzyme in the purine biosynthetic pathway. The resultant double deletion strain (ΔrfbU ΔpurE) was designated WRRP1. The DNA flanking the transposon insertion was sequenced to determine the open reading frame that had been interrupted to cause the rough phenotype and was found to be rfbU. The complete sequence of Brucella rfbU is described for the first time in this application in SEQ ID NO:1.

Unlike the rough mutants of the present invention, none of the rough mutants described previously including *B. abortus* strain 2308 rfbU mutant, VTRA1, and the VTRA1 transposon mutation integrated into the chromosomes of *B. melitensis* and *Brucella suis* by allelic exchange to create VTRM1 and VTRS1, respectively [McQuiston, J. R. et al. (1995) Abstract, CRWAD, November 1995; Winter, A. J. et al. (1996) *Am. J. Vet. Res.* 57:677-683] contained a defined mutation. In other words, the previously described mutant strains were produced by a transposon insertion which is a random event and can occur at any chromosomal location wherein the mutants of the present invention were produced by a directed allelic exchange to produce a unrevertable, defined deletion in the gene. A plasmid construct containing a synthetic copy of the putative rfbU gene that restored the smooth phenotype to the WRR51 deletion mutant of the present invention, did not restore the smooth phenotype to the VTRA1 transposon mutant. The inability to complement the transposon mutant indicates either that the transposon insertion confers a more general genetic defect in LPS biosynthesis (via a polar effect), or that the VTRA1 strain has additional mutations that affect LPS biosynthesis. The rough mutants of the present invention have a defined, nonreverting, deletion in the putative rfbU gene that was integrated into the chromosome by allelic exchange.

In order to construct the deletion in a rough strain, several factors had to be considered. The sequence of the flanking DNA (the rfbU gene) extending far enough in either direction of the deletion had to be known to allow for PCR or direct cloning of a large enough region of the Brucella chromosome. In addition, it was important to allow for a deletion of a significant portion of the rfbU gene to inactivate the gene in the first attempt; the actual crossover (allelic exchange) of the ΔrfbU for the wild type was very difficult because it occurred at a very low frequency, and after several trials, it was found that a threshold of at least 500 bp on either side of the deletion was necessary for efficient homologous recombination crossover in the Brucella chromosome. High biocontainment facilities, Biosafety Level 3 (BSL3), were necessary to move the deletion construct back into Brucella to make the mutant. Introducing the deletion construct required development of a more efficient method for electroporating DNA into Brucella than used before.

Therefore, it is an object of the present invention to provide a rfbU DNA fragment encoding 2693 nucleotides useful as a diagnostic agent.

It is another object of the present invention to provide an amino acid sequence for RfbU protein encoding 411 amino acids.

It is another object of the present invention to provide a Brucella rfbU DNA fragment containing a deletion useful in attenuating a Brucella strain.

It is another object of the invention to provide a recombinant vector comprising a vector and any of the above described DNA fragments.

It is a further object of the present invention to provide a host cell transformed with any of the above-described recombinant DNA constructs.

It is another object of the present invention to provide a method for producing RfbU protein which comprises culturing a host cell under conditions such that a recombinant vector comprising a vector and the rfbU DNA fragment is expressed and RfbU protein is thereby produced, and isolating RfbU protein for use as a diagnostic agent.

It is a further object of the present invention to provide an antibody to the above-described RfbU for use as a diagnostic agent.

It is yet another object of the invention to provide a Brucella spp. vaccine comprising an attenuated rough Brucella containing a defined deletion in the rfbU gene and effective for the production of antigenic and immunogenic response resulting in the protection of an animal against brucellosis. All of the Brucella which infect humans are highly related, probably biovars of the same species [Corbel, M. J. (1997) Emerging Inf. Dis. 3:213-221]. It is expected that this live vaccine would provide cross protection against other Brucella strains since there is thought to be high homology in the rfbU gene in brucellae [Jimenez de Bagues, M. P. et al. (1994) Infect. and Immun. 62:4990-4996].

It is a further object of the invention to provide a multivalent Brucella vaccine comprising defined Brucella rfbU mutants from a variety of strains effective for the production of antigenic and immunogenic response resulting in the protection of an animal against infection with brucellae.

It is yet another object of the present invention to provide a method for the diagnosis of brucellae infection comprising the steps of:

(i) contacting a sample from an individual suspected of having the infection with antibodies which recognize RfbU protein; and (ii) detecting the presence or absence of a complex formed between RfbU and antibodies specific therefor.

It is yet another object of the present invention to provide a method for the diagnosis of Brucella in a sample using the polymerase chain reaction, said method comprising:

(i) extracting DNA from the sample;
(ii) contacting said DNA with
 (a) at least four nucleotide triphosphates,
 (b) a primer that hybridizes to rfbU DNA, and
 (c) an enzyme with polynucleotide synthetic activity,
under conditions suitable for the hybridization and extension of said first primer by said enzyme, whereby a first DNA product is synthesized with said DNA as a template therefor, such that a duplex molecule is formed;

(iii) denaturing said duplex to release said first DNA product from said DNA;

(iv) contacting said first DNA product with a reaction mixture comprising:
 (a) at least four nucleotide triphosphates,
 (b) a second primer that hybridizes to said first DNA, and
 (c) an enzyme with polynucleotide synthetic activity,
under conditions suitable for the hybridization and extension of said second primer by said enzyme, whereby a second DNA product is synthesized with said first DNA as a template therefor, such that a duplex molecule is formed;

(v) denaturing said second DNA product from said first DNA product;

(vi) repeating steps iii-vi for a sufficient number of times to achieve linear production of said first and second DNA products;

(vii) fractionating said first and second DNA products generated from said rfbU DNA; and (viii) detecting said fractionated products for the presence or absence of rfbU in a sample.

It is yet another object of the present invention to provide a method for the detection of Brucella spp. in a sample which comprises assaying for the presence or absence of rfbU RNA or DNA in a sample by hybridization assays.

It is a further object of the present invention to provide a diagnostic kit comprising a RfbU antibody and ancillary reagents suitable for use in detecting the presence of brucellae in mammalian tissue or serum.

It is a further object of the present invention to provide a diagnostic kit comprising primers specific for the amplification of rfbU sequences and ancillary reagents suitable for use in detecting the presence of brucellae in mammalian tissue or serum.

It is yet an object of the present invention to provide a therapeutic method for the treatment or amelioration of symptoms of brucellosis, said method comprising providing to an individual in need of such treatment an effective amount of sera from individuals immunized with the vaccine strains of the present invention in a pharmaceutically acceptable excipient.

It is another object of the present invention to provide a means to express antigens of interest as potential therapeutics or vaccines for human and veterinary use. RfbU is usually either cytoplasmic or associated with the inner membrane. When brucellae are lysed within host cells, RfbU and any antigen designed to be expressed with RfbU would then be accessible to the intracellular environment of the cell or host.

It is another object of the invention to provide an inactivated vaccine produced from the live attenuated Brucella described above. The attenuated Brucella of the present invention can be used in producing inactivated Brucella vaccines. By using an attenuated Brucella, particularly the double mutant which is significantly attenuated, there is a much greater margin of safety in the event that the product is incompletely inactivated. Starting with an attenuated strain is also much safer during the manufacturing phase, and may allow production under lower biocontainment levels. In addition, inactivated attenuated Brucella strains can be used to isolate subunits for subunit vaccines.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1:
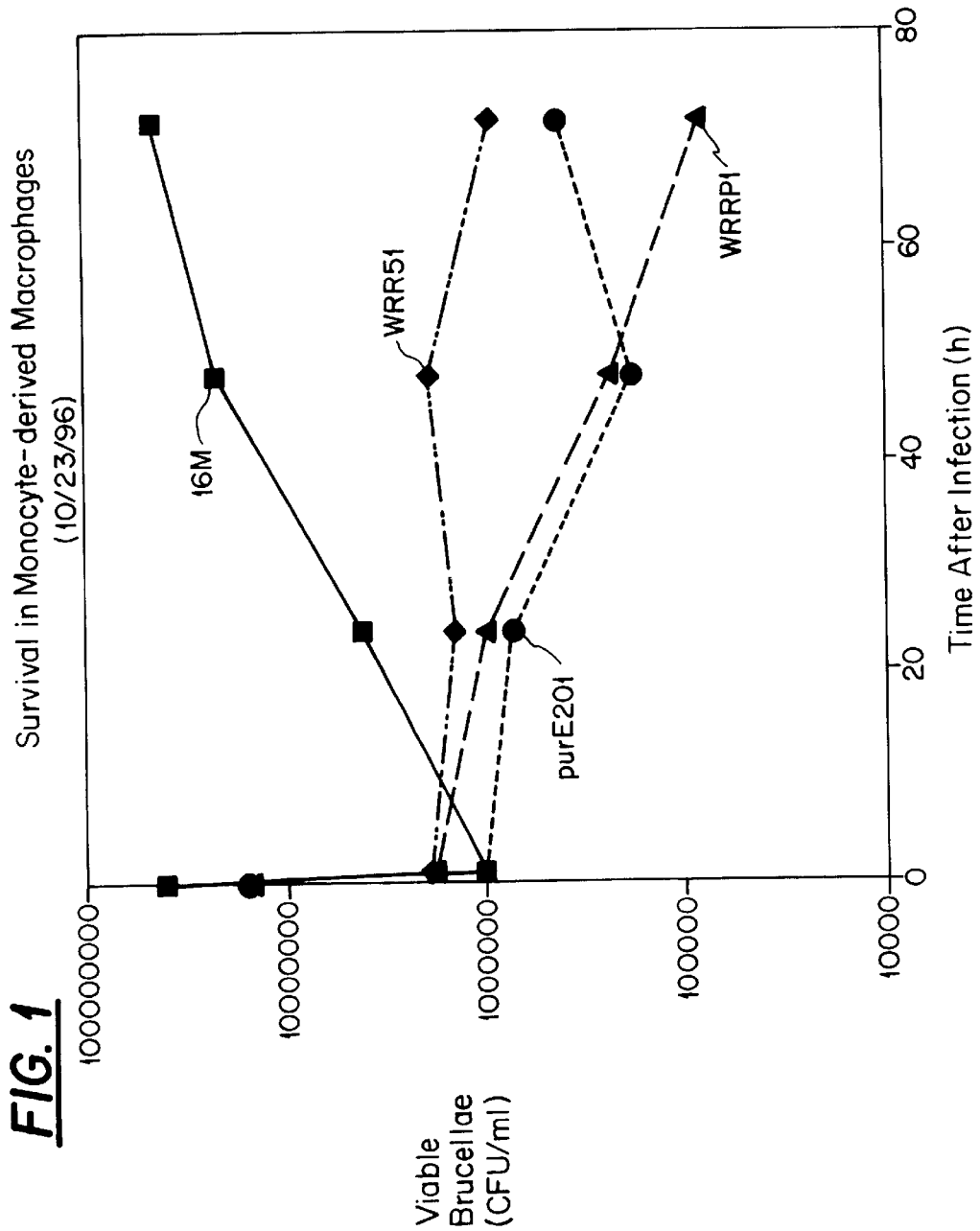
FIG. 1 shows ability of rough mutants to grow within human host cells.
Figure 2:
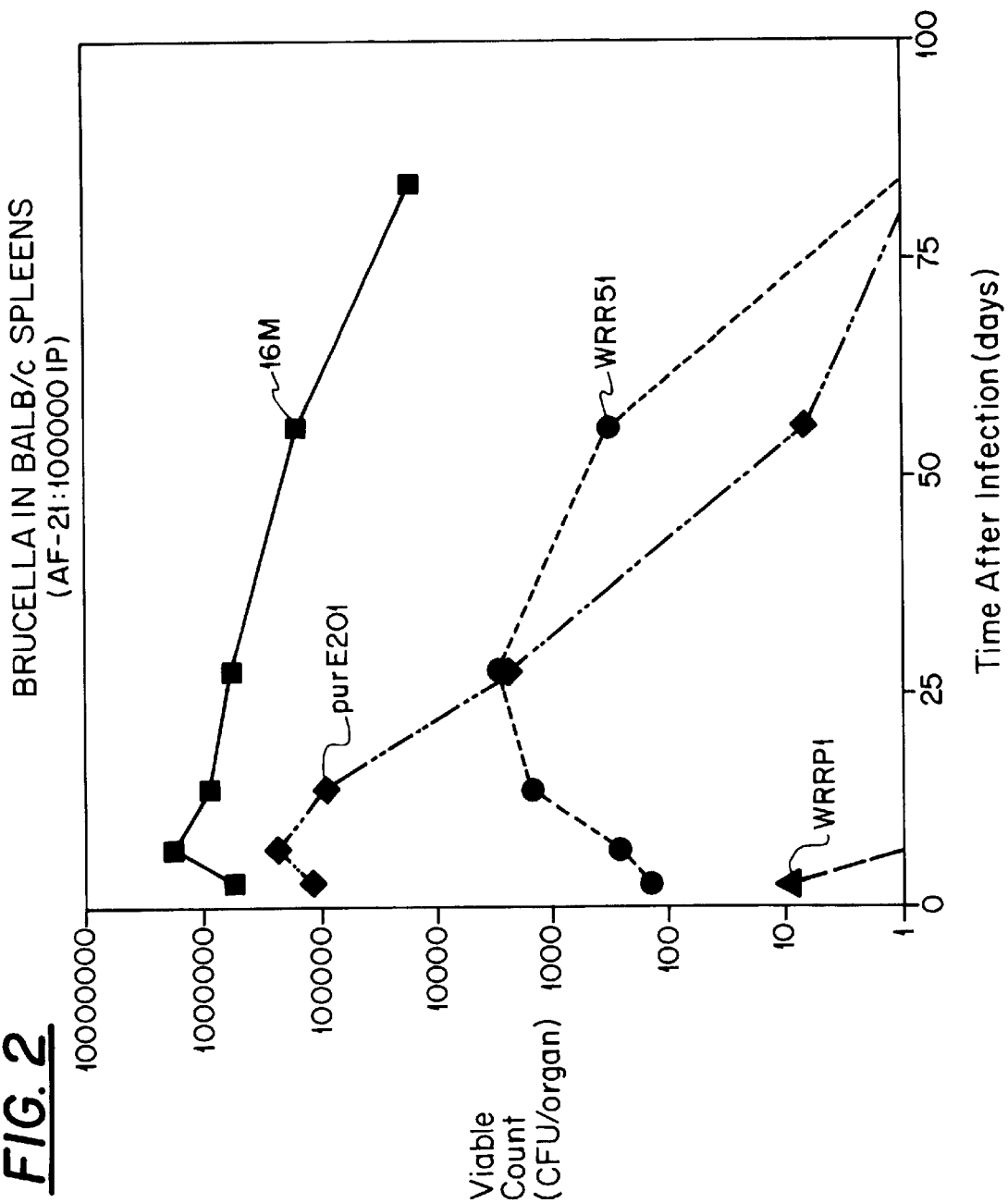
FIG. 2 shows the ability of rough mutants to infect mice via the intraperitoneal route.

In one embodiment, the present invention relates to a DNA or cDNA segment which encodes RfbU, a mannosyltransferase. The sequence of the gene, specified in SEQ ID NO:1, was obtained by cloning out a Brucella abortus VTRA1 chromosome containing a Tn5 transposon and sequencing the subclones to determine the insertion site of Tn5 in the VTRA1 chromosome. The sequenced gene fragment comprising 2693 base pairs contains an open reading frame of 1233 base pairs.

DNA or polynucleotide sequences to which the invention also relates include sequences of at least about 6 nucleotides, preferably at least about 8 nucleotides, more preferably at least about 10-12 nucleotides, most preferably at least about 15-20 nucleotides corresponding, i.e., homologous to or complementary to, a region of the rfbU nucleotide sequence. Preferably, the sequence of the region from which the polynucleotide is derived is homologous to or complementary to a sequence which is unique to the rfbU gene. Whether or not a sequence is unique to the rfbU gene can be determined by techniques known to those of skill in the art. For example, the sequence can be compared to sequences in databanks, e.g., GenBank and compared by DNA:DNA hybridization. Regions from which typical DNA sequences may be derived include but are not limited to, for example, regions encoding specific epitopes, as well as non-transcribed and/or non-translated regions.

DNA sequences also embodied in the present invention include the rfbU sequence containing a deletion. The exemplified deletion described below in the Examples is 607 base pairs in length, spanning from position 1063 to position 1670 of the DNA sequence identified in SEQ. ID. NO:1 and was chosen because of conveniently located restriction sites. Other deletions of any size can be introduced into the rfbU gene for different purposes. In the case where RfbU function is to be eliminated, a deletion large enough to eliminate any possibility of recombinational restoration of gene function is preferable. The deletion need not be framed by restriction sites and can be introduced by PCR, for example. However, cloned homologous DNA of about 500 base pairs flanking the deletion site is necessary for efficient allelic replacement. Methods for manipulating genes in Brucella are known in the art, please see e.g., Maniatis, Fritsch and Sambrook, *Molecular Cloning: a Laboratory Manual* (1982) or *DNA Cloning*, volumes I and II (D. N. glover ed. 1985) or *Current Protocols in Molecular Biology*, Ausubel, F. M. et al. (Eds.) John Wiley & Sons, Inc., for general cloning methods.

The derived polynucleotide is not necessarily physically derived from the nucleotide sequence shown in SEQ ID NO:1, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays and for the discovery of other rfbU sequences.

In another embodiment, the present invention relates to a recombinant DNA molecule that includes a vector and a DNA sequence as described above. The vector can take the form of a plasmid, such as pUC19, or any other vector which replicates in *E. coli*, or a suicide vector, or broad host range vectors for example pTh10(IncP), pSa(IncW) and R751 (IncP) [Rigby, C. E. and A. D. E. Fraser (1989) *Can. J. Vet. Res.* 53:326-330] and others known in the art.

In a further embodiment, the present invention relates to host cells stably transformed or transfected with the above-described recombinant DNA constructs. The host cell can be any Brucella or other host cell for which the vector is designed. The vector containing the rfbU gene is expressed in the bacteria and the product can be isolated for use in diagnostic assays. For example, the plasmid pRFBU1, described below in Materials and Methods, containing the rfbU/cat construct can be electroporated into other brucellae, and by allelic exchange with the wild type form of rfbU, can attenuate the electroporants. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. The DNA sequence can be present in the vector operably linked to a highly purified IgG molecule, an adjuvant, a carrier, or an agent for aid in purification of RfbU protein. The transformed or transfected host cells can be used as a source of DNA sequences described above. When the recombinant molecule takes the form of an expression system, the transformed or transfected cells can be used as a source of the protein described below.

In another embodiment, the present invention relates to a RfbU protein having an amino acid sequence corresponding to SEQ ID NO:2 and encompassing 411 amino acids or any allelic variation thereof.

A polypeptide or amino acid sequence derived from the amino acid sequence in SEQ ID NO:2, refers to a polypeptide having an amino acid sequence identical to that of a polypeptide encoded in the sequence, or a portion thereof wherein the portion consists of at least 2-5 amino acids, and more preferably at least 8-10 amino acids, and even more preferably at least 11-15 amino acids, or which is immunologically identifiable with a polypeptide encoded in the sequence.

A recombinant or derived polypeptide is not necessarily translated from a designated nucleic acid sequence, or the sequence in SEQ ID NO:1; it may be generated in any manner, including for example, chemical synthesis, or expression of a recombinant expression system. In addition the polypeptide can be fused to other proteins or polypeptides for example, any protective antigen of any pathogen, bacterial or viral for secretion of heterologous antigens from within the host cell since RfbU is either cytoplasmic or associated with the inner membrane. In addition, the protein or polypeptide can be fused to other proteins or polypeptides which increase its antigenicity, thereby producing higher titers of neutralizing antibody when used as a vaccine. Examples of such proteins or polypeptides include any adjuvants or carriers safe for human use, such as aluminum hydroxide.

In another embodiment, the present invention relates to antibodies specific for the above-described RfbU protein. For instance, an antibody can be raised against the complete RfbU protein or against a portion thereof. Persons with ordinary skill in the art using standard methodology can raise monoclonal and polyclonal antibodies to the polypeptide of the present invention. Material and methods for producing antibodies are well known in the art (see for example Goding, in, *Monoclonal Antibodies: Principles and Practice*, Chapter 4, 1986).

In a further embodiment, the present invention relates to a method for detecting the presence of brucellosis infection or antibodies against Brucella in a sample. Using standard methodology well known in the art, a diagnostic assay can be constructed by coating on a surface (i.e. a solid support) for example, a microtitration plate or a membrane (e.g. nitrocellulose membrane), all or a unique portion of the RfbU protein, or alternatively, inactivated attenuated Brucella described above, and contacting it with the serum of a person suspected of having a brucellosis infection. The presence of a resulting complex formed between the antigen (RfbU or attenuated Brucella) and antibodies specific therefor in the serum can be detected by any of the known methods common in the art, such as fluorescent antibody spectroscopy or colorimetry. This method of detection can be used, for example, for the diagnosis and typing of brucellosis infections.

In yet another embodiment, the present invention relates to a method of detecting the presence of Brucella in a sample. Using standard methodology well known in the art, a diagnostic assay can be constructed by coating on a surface (i.e. a solid support) for example, a microtitration plate or a membrane (e.g. nitrocellulose membrane), antibodies specific for RfbU, and contacting it with serum or tissue sample of a person suspected of having a brucellosis infection. The presence or absence of a resulting complex formed between RfbU in the serum or presented on antigen presenting cells and antibodies specific therefor can be detected by any of the known methods common in the art, such as fluorescent antibody spectroscopy or colorimetry. This method of detection can be used, for example, for the diagnosis of a brucellosis infection or for typing the specific Brucella bacteria causing such an infection.

In another embodiment, the present invention relates to a diagnostic kit which contains RfbU from a specific strain or species of Brucella or several different strains and species of Brucella and ancillary reagents that are well known in the art and that are suitable for use in detecting the presence of antibodies to Brucella in serum or a tissue sample. Tissue, blood, serum, or urine samples contemplated can be animal, in particular abortion products of large animals, or human, or other vertebrates. Other samples contemplated include dairy products, especially unpasturized products, from which the disease is most frequently contracted.

In yet a further embodiment, the present invention relates to DNA or nucleotide sequences for use in detecting the presence or absence of Brucella using the polymerase chain reaction (PCR). Since rfbU is probably very similar at the DNA level across all Brucella, the DNA sequence of the present invention can be used to design primers which specifically bind to the rfbU DNA for the purpose of detecting the presence, absence, or quantitating the amount of Brucella. The primers can be any length ranging from 7-40 nucleotides, preferably 10-15 nucleotides, most preferably 18-25 nucleotides. Reagents and controls necessary for PCR reactions are well known in the art. The amplified products can then be analyzed for the presence or absence of rfbU sequences, for example by gel fractionation, with or without hyridization, by radiochemistry, and immunochemical techniques. This method can also be used for typing a brucellosis infection.

In yet another embodiment, the present invention relates to a diagnostic kit which contains PCR primers specific for rfbU, and ancillary reagents that are well known in the art and that are suitable for use in detecting the presence or absence of Brucella in a sample using PCR. Samples contemplated can be human or other mammals, dairy products, blood, urine, tissues, depending on the stage of infection. Early infection tissues would include lungs and the lymphatic system, late infection tissues would include spleen, liver, and kidneys, and later infection tissues would include bone marrow and absesses in organs and brain.

In another embodiment, the present invention can be used to diagnose Brucella infection by using the DNA sequences for detecting the presence or absence of rfbU in a DNA sample using hybridization assays such as Southern hybridization or the expression of rfbU gene, or rfbU RNA, by northern hybridizations and other hybridization assays well known to a person with ordinary skill in the art.

In another embodiment, the present invention relates to a vaccine for protection against infections by Brucella. The vaccine comprises one or more attenuated rough Brucella strains containing a defined deletion, for example, in the rfbU gene. The deletion in the rfbU gene can be introduced by allelic exchange due to a double cross-over recombinational event, or any other method wherein a DNA replacement event in which two separate DNA recombination events result in the exchange of a piece of the intact gene for a homologous piece containing a deletion. The deletion is preferably large enough such that the gene is inactivated in the first attempt and to reduce the likelihood of a recombinational repair. Other genes which can be deleted include purE, dnaKJ, recA, groELS, catalase, or any other gene which contributes to survival in human macrophages and/or to bacterial virulence. Any strain of Brucella can be used to introduce such an attenuating mutation. The resulting attenuated strain can be tested for the deletion of the targetted gene by methods known in the art such as Southern blot hybridization, and the level of attenuation tested in a mouse model as described in the Examples below. Any deletion in the rfbU gene would result in the attenuation of the bacteria unless the deletion was small and allowed for functional rfbU expression. Any deletion which inactivates the rfbU gene expression or blocks function of its gene product will be both rough and attenuated.

For example, as described below in more detail, a deletion in the rfbU gene of *Brucella melitensis* was introduced by allelic exchange with a copy of the rfbU gene present on a vector. The rfbU gene to be exchanged with the wild type version contained a deletion into which a chloramphenicol acetyl transferase gene was cloned. Once the vector was introduced into *B. melitensis*, by electroporation in this example, a double cross-over recombinational event occured such that the vector rfbU gene containing the deletion, was exchanged for the chromosomal wild type rfbU. The resulting *B. melitensis* strain WRR51 contained a defined mutation was rough and attenuated, and did not possess resistance to an antibiotic used to treat brucellosis.

In another embodiment of the invention, the Brucella having the deletion in the rfbU gene as described above additionally contains another deletion in a different gene. The advantage of having two deletions is to further reduce the possibility of reversion, and to additionally attenuate the bacteria. However, for use as a live vaccine a certain amount of replication is necessary in the host. Therefore, any vaccine strain designed in the methods of the present invention must be tested for its ability to survive in the host. These tests can be done in vitro, for example in a monocyte-derived macrophages system as described below in the Examples, or, as a second step, in non-human primates. It is preferable that the bacteria persists in the host for sufficient time to elicit a strong immunogenic response, for example from about four to six weeks. Bacteria too attenuated to survive enough to elicit an immunogenic response can be useful as diagnostic agents.

In the specific examples described below, a deletion in the purE gene of *B. melitensis* WRR51 was introduced using the allelic exchange procedure described above. The wild type purE locus was replaced with a deleted allele with a kanamycin resistance cassette inserted in the deletion site. The resultant double deletion strain (ΔrfbU ΔpurE) was designated WRRP1. Other genes which can be used for introducing a second deletion include, but are not limited to e.g. dnaKJ, recA, genes potentially contributing to intracellular survival and proliferation (replication), for example by studying genes homologous to those found important in other intracellular bacterial pathogens or by screening for important genes for brucellar intracellular survival directly using IVET, or in vivo expression technology [Mahan, M. J. et al. (1993) *Science* 259:686-688].

Both the single deletion strain, WRR51, and the double deletion strain, WRRP1, were tested in human-derived macrophages and were found able to infect human monocytes, and had reduced capacity to grow within host cells. WRRP1, the double deletion, appeared to lose viability in host cells at a more rapid rate than those with a single deletion mutation such as WRR51, (ΔrfbU), or *B. melitensis* ΔpurE. Thus, the subject strains should be able to persist in the host for extended periods of time, usually weeks, to enhance the effectiveness of the immunizing effect by continuous stimulation of the host immmune system until the host immune system has cleared all the organisms.

Ideally, for human administration, the vaccine strains should be sensitive to all antibiotics and synthetic antibacterials which are active against strains of Brucella. Even though strains containing these markers can be used as animal vaccines, it is preferable that strains selected on the basis of a selectable markers such as cat or kanamycin be further manipulated to remove these selectable markers. Methods for removing the marker gene include use of a "toxic" gene in vector as counterselectable marker to insure double crossover event e.g. sacB. These markers would be removed by a second allelic exchange, homologous recombination, this time with a copy of the gene containing the same deletion, but without the antibiotic resistance cassette inserted and verified by phenotype screening and Southern blot analysis. It is preferable to avoid providing resistance genes that can be disseminated through the environment or within the host to other pathogens.

The subject vaccines may be used in a wide variety of vertebrates. The subject vaccines will find particular use with mammals such as man and domestic animals. Domestic animals include bovine, ovine, porcine, equine, caprine, domestic fowl, Leporidate e.g., rabbits, or other animal which may be held in captivity or may be a vector for a disease affecting a domestic animal such as a marine mammal.

The purified vaccine solution is prepared for administration to mammals by methods known in the art, which can include filtering to sterilize the solution, diluting the solution, adding an adjuvant and stabilizing the solution. The vaccine can be lyophilized to produce a vaccine against brucellae in a dried form for ease in transportation and storage. Further, the vaccine may be prepared in the form of a mixed vaccine which contains the deletion strains as described above and at least one other antigen as long as the added antigen does not interfere with the effectiveness of the vaccine and the side effects and adverse reactions are not increased additively or synergistically.

The vaccine may be stored in a sealed vial, ampule or the like. The present vaccine can generally be administered in the form of a liquid or suspension. In the case where the vaccine is in a dried form, the vaccine is dissolved or suspended in sterilized distilled water before administration. Generally, the vaccine may be administered orally, subcutaneously, intradermally or intramuscularly but preferably intranasally in a dose effective for the production of neutralizing antibody and protection from infection or disease. The manner of application of the vaccines may be varied widely, any of the conventional methods for administering a live vaccine being applicable. These include, orally, on a solid physiologically acceptable base, or in a physiologically acceptable dispersion. The dosage of the vaccine (number of bacteria, number of administrations) will depend on route of administration and will vary according to the species to be protected.

When providing a patient with live bacteria vaccines, the dosage of administered agent will vary depending upon such factors as the route of administration, patient's species, age, weight, height, sex, general medical condition, previous medical history, etc. In general, it is desirable to provide the recipient with a dosage of the above compounds which is in the range of from about 10 cfu/kg to $10^6$ cfu/kg (body weight of patient), although a lower or higher dosage may be administered. For calves, for example, administration of live bacteria can be by intramuscular injection of by feeding in doses which are safe and may be appropriate. For example, at 10 months of age, heifers can be injected subcutaneously in the axillary area with $1-1.4\times10^{10}$ cfu [Cheville, N. F. et al. (1993) *Am. J. Vet. Res.* 54:1591-1597]. One or more additional administrations may be provided as booster doses, usually at convenient intervals such as two to three weeks.

In another embodiment, the present invention related to a method and composition for delivering antigens or genes into cells. One or more of the desired antigens, or genes coding for these antigens, can be introduced into the live brucellae strains described above for use as a vaccine, and can be used only to provide said antigen, i.e. as a delivery vehicle, or to provide protection as a vaccine and deliver the desired antigen. The desired gene or antigen can be introduced into the bacteria either as episomal DNA, or as part of the Brucella chromosome by recombination for example, advantageously inserted in the deletion site of the vaccine strain, or replacing the selectable marker used in selecting the vaccine strain. Genes of interest may come from diverse sources, such as bacteria, viruses, fungi, protozoa, metazoan parasites or the like. The structural genes may encode envelope proteins, capsid proteins, surface proteins, toxins, such as exotoxins or enterotoxins, or the genes of interest may specify proteins, enzymes, or oligosaccharide antigen or for modification of a saccharide-containing antigen, such as LPS, of the host bacterial strain, or for synthesis of a polypeptide antigen. Specific examples of genes of interest include HIV vif, malarial circumsporozoite protein, HBV core protein, and arboviral coat protein, to name a few. The construct or vector containing the gene of interest may be introduced into the host strain by any convenient means such as conjugation, transformation, transfection, transduction, etc. The Brucella containing the gene or antigen of interest is then allowed to enter the cell by infection, wherein the bacteria can replicate for a limited time thereby providing the antigen or gene of interest inside the cell. Additional administrations of the antigen or gene of interest can occur depending on the amount of antigen desired in the infected cell.

Described below are examples of the present invention which are provided only for illustrative purposes, and not to limit the scope of the present invention. In light of the present disclosure, numerous embodiments within the scope of the claims will be apparent to those of ordinary skill in the art.

The following MATERIALS AND METHODS were used in the examples that follow.

Strains and growth conditions. All Brucella strains were grown in brucella broth or agar or M9 minimal agar. *B. melitensis* strains 16M (wild type), ΔpurE201 [Drazek et al. (1995) *Infect. Immun.* 63:3297-3301], WRR51 and WRRP*1* were used to infect both monocyte-derived macrophages (MDMs) and mice. Stocks of exponential-phase cultures frozen in 20% glycerol were thawed and used to inoculate. Broth cultures were shaken at 37° C. for 22 to 26 hours until an $A_{600}$ of 0.4 to 0.6 was obtained. Bacterial cells were then harvested by centrifuge, washed in sterile 0.9% NaCl, and adjusted to the correct dilution in the same. Turbidity was measured by spectrophotometer (Spectronic 20, Spectronic Instruments, Inc., Rochester, N.Y.) to estimate viable bacterial counts and thus determine the appropriate dose for infection. Actual colony-forming units (CFUs) in the inocula were determined by serial dilution and plating on Brucella agar. Plate counts were made after four days of incubation at 37° C., unless otherwise noted.

Animals. BALB/C female mice were obtained from Harlan Sprague Dawley, Frederick, Md., and were used at eight to twelve weeks of age. Mice were Brucella-free and were kept in a Biosafety level three (BSL-3) facility. Studies were performed according to Armed Forces Institute of Pathology Regulation 70-1 and all regulations and guidelines regarding the use of laboratory animals in research.

Construction of *B. melitensis* rough mutants. The DNA sequence of pJM63 [Winter, A. J. et al. (1996) *Amer. J. Vet. Res.* 57:677-683] flanking the Tn5 insertion in the putative rfbU gene of *B. abortus* 2303 was obtained. The rfbU gene was subcloned, and two ClaI sites were used to delete an internal portion of the gene (between positions 1063 and 1670) containing the Tn5 insertion, to create pJM83ΔClaI. A chloramphenicol resistance cassette was then place into the ClaI deletion site to make the mutator plasmid pRFBU1. *Brucella melitensis* 16M was grown for 20 hours in YENB [Sharma, R. C., and R. T. Schimke (1996) *BioTechniques* 20:42-44], pelleted, washed in ½ volume cold 10% glycerol and resuspended in 1/10 volume of the same. In cuvettes 1 μg of plasmid DNA was added to 100 μof the electrocompetent bacteria and then electroporated at 2.5 kV, 25 μF and 600 Ω. One ml of SOC (Life Technologies, Inc., Gaithersburg, Md.) was added and the mix was incubated at 37° C. with shaking for one hour. The electroporation mix was then plated on brucella agar containing 10 μg chloramphenicol per ml.

Chloramphenicol-resistant electroporants were then screened on brucella agar plates containing 100 μg/ml ampicillin and on plates with 5 μg/ml chloramphenicol and 50 μg/ml ampicillin. Ampicillin-sensitive, chloramphenicol-resistant colonies were then tested for changes in LPS first by staining with crystal violet and then by agglutination with anti-brucellar LPS serum. The chromosomes of these transformants were isolated [Marmur, J. (1961) *J. Mol. Biol.* 3:208-218] and examined by Southern hybridization. Chromosomal DNA preparations were digested with EcoRI and ClaI, electroporated on a 1% agarose slab gel in TAE buffer, and transferred in a positive pressure cell (Stratagene, LaJolla, Calif.) to a Nytran membrane (Schleicher and Schuell, Keene, N.H.). An rfbU probe was made by DNA amplification via the polymerase chain reaction (PCR) using oligonucleotide primers with the nucleotide sequences 5'-GGATGTCGACCCAGCCCTCCACATCAATAGC-3' (SEQ ID NO:3) and 5'-TTGCGGATCCTTTACTCGTCCGTCTCTTAC-3' (SEQ ID NO:4). *B. melitensis* 16M DNA served as template. The amplicon contained the rfbU gene, 606 bp of the upstream flank and 278 bp of the downstream flank. The probe was labeled nonisotopically (Amersham Life Sciences, Birminghamshire, England) and hybridised at 42° C.

Genetic complementation was used to confirm that the ΔrfbU 5.1 mutation caused the LPS defect in WRR51. The amplicon described above that contained an intact copy of rfbU was cloned into pBBR1MCS and the resultant construct was electroporated into WRR51. Presence of the plasmid in electroporants was verified by antibiotic selection and by plasmid isolation and analysis. WRR51 electroporants bearing the rfbU plasmid were tested for restoration of wild type LPS synthesis by crystal violet staining and by anti-LPS agglutination.

*B. melitensis* strain WRRP1 was constructed by electroporating WRR51 with pURE198 [Drazek et al. (1995) *Infect. Immun.* 63:3297-3301]. Electroporants with resistance to kanamycin (50 μg/ml) and chloramphenicol (5 μg/ml) were selected on brucella agar plates and then replica plated on brucella agar containing 100 μg/ml ampicillin, M9 minimal media agar and M9 agar with added purines (5 mM adenine, 0.3 mM guanine). Recombinational replacement of the purE locus with ΔpurE198 was confirmed by Southern hybridisation. Chromosomal preparations were digested with EcoRI and HindIII and probed with a PCR amplification product that included most of the purEK operon (GenBank locus BMU10241) and was made using the oligonucleotide primers 5'-CACCATGCAGCCGACACA-3' (SEQ ID NO:5) and 5'-CCGCGCCGCAGATTCAGG-3' (SEQ ID NO:6). Maintainance of the ΔrfbU5.1 mutation in WRRP1 was also verified by Southern blot.

Procedures not specified above were done by standard methodology [Ausubel et al. (ed.) 1994. Current protocols in molecular biology. Greene Publishing Associates, New York; and Sambrook et al. 1989. Molecular cloning: a laboratory manual, 2nd ed. Cold Spring Harbor, N.Y.].

Human MDM infection. Mononuclear cells obtained by centrifuging leukopaks from normal donors over lymphocyte separation medium (Organon Teknika, Durham, N.C.). Counterflow centrifugal elutriation was then used to further purify the monocytes [L. M. Wahl et al. (1984) *Cell. Immunol.* 85:373-383], resulting in preparations with greater than 95% viability (estimated by trypan exclusion) and <10% lymphocytes. Monocytes were suspended in MDM medium [RPMI 1640 medium (Life Technologies, Inc., Gaithersburg, Md.) with 10% heat-inactivated human serum (Sigma Chemical Co., St. Louis, Mo.), 2 mM L-glutamine and 10 ng/ml of recombinant human macrophage colony stimulating factor (Jay Stoudemire, Genetics Institute, Boston, Mass.)]. This suspension was added to wells in a sterile tissue culture plate and $10^5$ cells per well were cultured as adherent monolayers at 37° C. in a 5% $CO_2$ incubator. On the fourth day and again on the seventh day, half of the medium was removed and replaced with fresh medium. On the eighth day of the experiment, the media in the MDM culture wells was removed and replaced with the medium described above, except with 10% unheated normal serum in place of Sigma serum. Brucella strains were grown as stated above. Broth media did not contain antibiotics to avoid carryover; cultures used to infect were plated selective and nonselective agar to verify that antibiotic resistance was maintained uniformly in strains which bear these markers. After the saline wash, brucellae were resuspended to $2 \times 10^8$ CFU/ml in saline and added to MDM wells at a multiplicity of infection of 10:1. Infections proceeded for 60 min. at 37° C., then monolayers were washed three times with RPMI with 10% Sigma serum and 2 mM L-glutamine. MDM medium with 1 µg/ml gentamycin was then added to wells and plates were incubated at 37° C. in a 5% $CO_2$ incubator. At various timepoints plates were removed and MDM monolayers were washed as before, and then lysed by adding 0.1% Triton X-100 and mixing vigorously. Lysates were diluted serially in sterile saline, and these dilutions were plated on brucella agar to obtain viable counts. Presented here are mean values from three MDM wells, dilutions from each plated in duplicate. The data shown are representative of at least four different experiments.

Survival in mice. Groups of mice were inoculated intraperitoneally with various doses of *B. melitensis* 16M and of the mutants, or with 0.2 ml sterile saline in the case of the control group. Blood, spleens, liver and lungs were obtained from the infected and control mice at 3, 7, 14, 42, 56 and 84 days after infection. Three mice from each group were sampled at each timepoint. Organs were weighed and then homogenized with 1 ml sterile saline. Suspensions were then diluted in sterile saline and plated on brucella agar. Colonies of Brucella were counted after 4 days of incubation at 37° C., and then again after 6 days for slow-growing strains. The identity of recovered colonies was confirmed by screening for antibiotic resistance and relevant phenotype.

EXAMPLE 1

The *B. abortus* gene containing the Tn5 insertion was first cloned from the VTRA1 chromosome on an 11.6 kbp DNA fragment in the plasmid construct pJM63. From a number of subclones of the pJM63 insert, the nucleotide sequence of the 2693 bp region containing the transposon insertion was determined (SEQ. ID. NO: 1). The Tn5 insertion was located within an open reading frame of 1233 bp which coded for a gene that was distantly related (40% amino acid similarity) to the sequence of the *Salmonella enterica* LT2 RfbU. A deletion of 607 bp was made in the putative rfbU gene of pJM63 using ClaI restriction sites at nucleotide positions 1063 and 1670 in the DNA sequence. A 1053 bp cassette containing a chloramphenicol acetyl transferase gene (cat) was ligated into the deletion site to create the plasmid pRFBU1. pRFBU1 was electroporated into *B. melitensis* strain 16M and electroporants with pRFBU1 integrated were selected on Brucella agar containing chloramphenicol. Resistant colonies were then screened for the loss of ampicillin resistance, which indicated that the vector portion of pRFBU1 had been lost from the chromosome by a second crossover recombinational event. DNA hybridization confirmed that the chloramphenicol resistant and ampicillin sensitive electroporants had the deletion mutation carrying the chloramphenicol resistance cassette in place of the wild type chromosomal locus. The deletion strain, designated WRR51, was confirmed to be rough by staining with crystal violet and by lack of agglutination with an anti-LPS serum.

EXAMPLE 2

A purE deletion was then introduced into *B. melitensis* strain WRR51 by a similar allelic exchange procedure. The suicide vector pURE201 was used as previously described [Drazek, E. S. et al. (1995) *Infect. Immun.* 63:3297-3301] to replace the wild type purE locus with a deleted allele with a kanamycin resistance cassette inserted in the deletion site. The resultant double deletion strain (ΔrfbU ΔpurE) was designated WRRP1.

EXAMPLE 3

Human monocyte-derived macrophages were infected with *B. melitensis* 16M, with *B. melitensis* ΔpurE 201, and with rough mutants WRR51 and WRRP1 (FIG. 1). The wild type parent strain increased over two logs in 72 hours, but the rough mutants decreased in count over the same timecourse. Counts of the rough mutant WRR51 decreased gradually, comparable with levels seen with *B. melitensis* ΔpurE 201, while the rough purE strain, WRRP1, was reduced by a full log over 72 hours. These results indicated that though the rough mutants were fully able to infect human monocytes, they had a reduced capacity to grow within host cells. WRRP1 appeared to lose viability in host cells at a more rapid rate than WRR51 or *B. melitensis* ΔpurE 201.

EXAMPLE 4

In the murine model, BALB/c mice were infected intraperitoneally with $10^5$brucellae and spleen counts were taken at timepoints over 12 weeks (FIG. 2). Wild type *B. melitensis* 16M persisted in the spleens of infected mice for the full 12 weeks, increasing in count by a log in the first week and then gradually decreasing by about a log over the 11 weeks that followed. Spleens of mice infected with double mutant WRRP1 were fully cleared of viable bacteria by one week. Rough mutant WRR51 and *B. melitensis* ΔpurE 201 persisted in the spleen at eight weeks, but were cleared by 12 weeks. While these strains were similar in the duration of survival in the mouse spleen, early counts of the purE mutant were two logs higher than those of WRR51. This result indicated that the rough mutants are reduced in their efficiency to infect mice, at least by the intrapertoneal route. Both ΔpurE 201 and WRR51 were attenuated relative to the wild type *B. melitensis*, but both were able to survive in mice for over eight weeks. The double deletion mutant appeared to be severely attenuated compared to either of the single deletion mutants, but recent experiments indicate that increased dosage of WRRP1 can extend its persistence in mice to beyond four weeks.

What is claimed is:

1. An isolated Brucella DNA fragment havving the nucleotide sequence of SEQ ID NO: 1 modified to contain a non-reverting deletion of nucleotides from position 1063 to 1670, which fragment when stably inserted into a Brucella cell in a Brucella vaccine will result in a Brucella vaccine that does not cause seroconversion in a vaccinee exposrd thereto.

2. A recombinant DNA construct comprising:
   (i) a vector, and
   (ii) an isolated Brucella DNA fragment having the nucleotide sequence of SEQ ID NO: 1 modified to contain a stable non-reverting deletion of nucleotides from position 1063 to position 1670, which fragment when stably inserted into a Brucella cell in a Brucella vaccine will result in a Brucella vaccine that does not cause seroconversion in a vaccinee exposed thereto.

3. A recombinant DNA construct according to claim 2, wherein said vector is an expression vector.

4. The recombinant DNA construct according to claim 2, wherein said vector is a prokaryotic vector.

5. A host cell transformed with a recombinant DNA construct comprising:
   (i) a vector, and
   (ii) an isolated Brucella DNA fragment having the nucleotide sequence of SEQ ID NO:1 modified to contain a stable non-reverting deletion of nucleotides from position 1063 to position 1670, which fragment when stably inserted into a Brucella cell in a Brucella vaccine will result in a Brucella vaccine that does not cause seroconversion in a vaccinee exposed thereto.

6. A host cell according to claim 5, wherein said cell is prokaryotic.

7. The host cell according to claim 6, wherein said cell is Brucella.

8. A host cell according to claim 7, wherein said Brucella is *Brucella melitensis*.

9. Host cell WRRP1, having ATCC accession number PTA-3753.

10. Host cell WRR51, having ATCC accession number PTA-3754.

11. A method for producing which comprises culturing the host cell according to claim 5, under conditions such that said DNA fragment is expressed and said *Brucella* peptide is thereby produced, and isolating said *Brucella* peptide.

12. An isolated Brucella DNA fragment comprising the nucleotide sequence of SEQ ID NO: 1.

13. An isolated Brucella DNA fragment comprising at least 30 contiguous nucleotides of the nucleotide sequence of SEQ ID NO: 1.

* * * * *

UNITED STATES PATENT AND TRADEMARK OFFICE
CERTIFICATE OF CORRECTION

PATENT NO. : 6,444,445 B2 Page 1 of 1
APPLICATION NO. : 09/010877
DATED : September 3, 2002
INVENTOR(S) : Nikolich et al.

It is certified that error appears in the above-identified patent and that said Letters Patent is hereby corrected as shown below:

On Title page of the patent in the section (75) please replace the inventor's last name "McOulston" with --McQuiston--.

Signed and Sealed this

Seventeenth Day of July, 2007

JON W. DUDAS
*Director of the United States Patent and Trademark Office*